(12) United States Patent
Bedford

(10) Patent No.: US 11,298,258 B2
(45) Date of Patent: Apr. 12, 2022

(54) MANDIBULAR ADVANCEMENT DEVICE

(71) Applicant: SomnoMed Limited, Crows Nest (AU)

(72) Inventor: Christopher Bedford, Rozelle (AU)

(73) Assignee: SomnoMed Limited, Crows Nest (AU)

( * ) Notice: Subject to any disclaimer, the term of this patent is extended or adjusted under 35 U.S.C. 154(b) by 536 days.

(21) Appl. No.: 16/061,051

(22) PCT Filed: Oct. 14, 2016

(86) PCT No.: PCT/AU2016/000347
§ 371 (c)(1),
(2) Date: Jun. 11, 2018

(87) PCT Pub. No.: WO2017/106896
PCT Pub. Date: Jun. 29, 2017

(65) Prior Publication Data
US 2018/0360646 A1    Dec. 20, 2018

(30) Foreign Application Priority Data

Dec. 22, 2015 (AU) .............................. 2015905308

(51) Int. Cl.
*A61F 5/56* (2006.01)
*A61C 7/08* (2006.01)
(Continued)

(52) U.S. Cl.
CPC ............... *A61F 5/566* (2013.01); *A61C 7/08* (2013.01); *A61C 7/36* (2013.01); *A61C 9/0006* (2013.01)

(58) Field of Classification Search
CPC ...... A61F 5/566; A61F 5/56; A61F 2005/563; A61C 7/03; A61C 7/36; A61C 7/08;
(Continued)

(56) References Cited

U.S. PATENT DOCUMENTS

| 5,752,826 A | * | 5/1998 | Andreiko | ............. | A61C 9/0006 433/37 |
| 6,604,527 B1 | | 8/2003 | Palmisano | | |

(Continued)

FOREIGN PATENT DOCUMENTS

WO    WO 2014/043008 A1    3/2014

*Primary Examiner* — Caitlin A Carreiro
(74) *Attorney, Agent, or Firm* — DASCENZO GATES Intellectual Property Law, P.C.

(57) ABSTRACT

A mandibular advancement device includes a lower part, a lower flange, an upper part and an upper flange. The lower part is releasably attachable to at least a portion of a lower jaw. The lower flange has a lower engagement surface extending upwardly from the lower part. The upper part is releasably attachable to at least a portion of an upper jaw. The upper flange has an upper engagement surface extending downwardly from the upper part. The device includes a lower one way ratchet means configured to only allow uni-directional posterior movement of the lower flange relative to the lower part and/or an upper one way ratchet means configured to only allow uni-directional anterior movement of the upper flange relative to the upper part. When the device is fitted to a patient's jaws, the upper and lower engagement surfaces engage to cause anterior advancement of the lower jaw.

16 Claims, 14 Drawing Sheets

(51) Int. Cl.
*A61C 7/36* (2006.01)
*A61C 9/00* (2006.01)

(58) Field of Classification Search
CPC ........... A61C 7/10; A61C 9/0006; A61C 5/90;
A61C 9/00; A61C 19/006; A61C 19/045;
A61C 5/80; A61C 5/88; A63B 71/085
USPC ...... 128/848, 859, 861, 862; 433/6, 85, 140,
433/141, 149, 7, 68–69, 34, 37, 41, 42,
433/44, 72; 602/902
See application file for complete search history.

(56) References Cited

U.S. PATENT DOCUMENTS

| | | | |
|---|---|---|---|
| 2003/0207225 A1* | 11/2003 | Huge | A61C 7/10 433/7 |
| 2005/0028826 A1* | 2/2005 | Palmisano | A61F 5/566 128/848 |
| 2010/0261133 A1 | 10/2010 | Lax | |
| 2011/0030704 A1* | 2/2011 | Hanna | A61C 7/08 128/861 |
| 2011/0036357 A1* | 2/2011 | Abramson | A61F 5/566 128/848 |
| 2012/0145166 A1* | 6/2012 | Fallon | A61F 5/566 128/848 |
| 2012/0255563 A1 | 10/2012 | Thornton | |
| 2013/0081638 A1 | 4/2013 | Petelle et al. | |
| 2013/0112210 A1* | 5/2013 | Stein | A61F 5/566 128/848 |
| 2013/0160776 A1 | 6/2013 | Petelle et al. | |
| 2014/0072927 A1* | 3/2014 | Diaz | A61F 5/566 433/6 |
| 2014/0352701 A1 | 12/2014 | Ingemarsson-Matzen | |

* cited by examiner

MANDIBULAR ADVANCEMENT DEVICE

FIELD OF THE INVENTION

The present invention relates to a mandibular advancement device that has application in the treatment of snoring, obstructive sleep apnea (OSA) and certain temporomandibular joint disorders.

BACKGROUND OF THE INVENTION

It is generally thought that snoring and OSA occur when there is at least partial occlusion of the airway and that the tongue is involved in this. Snoring and OSA commonly occur during sleep. Mandibular advancement devices advance the lower jaw in an anterior direction, thereby carrying the tongue forward and reducing the likelihood of the tongue impacting on the airway. Numerous forms of mandibular advancement devices are known.

U.S. Pat. No. 6,604,527 discloses a mandibular advancement device having a lower bite block, with a pair of upwardly extending flanges, and an upper bite block, with a pair of downwardly extending flanges. The flanges each carry engagement surfaces. When the bite blocks are fitted to the jaws of a patient for use in sleep, the lower and upper engagement surfaces engage and cause anterior advancement of the lower jaw from the reflex path of opening and maintain that engagement and advancement whilst permitting movement, up to the normal range of jaw opening. This device is custom made for each patient from a desired cast of the patient's jaw. The position of the flanges on the bite blocks are fixed, so as to provide a set amount of jaw advancement for that particular patient. A major advantage of this device is that the jaws are not locked together, which means that the patient is able to speak, yawn and drink whilst wearing the device. The patient can also maintain a lip seal whilst wearing the device. This is essential to prevent the patient's mouth drying out during use, which causes significant discomfort and can lead to non-compliance. However, due to the device being custom manufactured for each patient, it is relatively expensive.

US patent application publication number US 2012/0255563 discloses a "universal" (i.e. one size fits all) mandibular advancement device. In this device, the upper and lower bite blocks are each a hard flat plastic frame with a tray of mouldable material thereon, the latter facing the patient's teeth. To fit the device to a patient, the bite blocks are placed in boiling water until the mouldable material softens. The bite blocks are then placed in the patient's mouth and the patient bites down to form an impression of their teeth. The teeth impressions are maintained in the bite blocks once they have cooled. The device includes a central, front mounted, screw type adjuster which is used to set the desired amount of advancement of the lower jaw. The universal fitment nature of the device makes is suited to mass production, which significantly reduces its cost compared to custom devices. However, a significant disadvantage of the device is the adjuster also locks the bite blocks, and thus the patient's jaws, together closed. This makes it difficult to speak, yawn or drink whilst wearing the device. In addition, the adjustment device protrudes outwardly from the user's mouth, breaking the lip seal. This can result in the patient's mouth drying out during sleep.

US patent application publication numbers US 2013081638 and US 20130160776 also disclose universal fitment type devices. These devices have bite blocks formed from a hard plastic shell, of a U-shaped cross section, with a mouldable insert therein. A disadvantage of these devices is that it is difficult to get a comfortable patient fit as the moulded insert often forms thin sharp edges which can cut the patient's mouth and jaw. It is difficult to manually trim any such sharp edges. Whilst it is possible to reheat and attempt to reshape the insert, it is difficult to push the insert back into the confines of the (U-shaped cross section) tray. The devices have a mechanism for adjusting the advancement of the lower jaw mounted to each side of the bite blocks. A disadvantage of this device is that the adjustment mechanisms are very difficult to use, which can lead to non-compliance. More particularly, adjustment involves manipulating, positioning and locking in place several small components. Further, whilst the adjustment mechanisms do have visible guides for the amount of adjustment, these guides are very hard to see. The adjustment mechanisms also lock the bite blocks/jaws together closed and thus also suffer from the inability to speak, yawn and drink disadvantages discussed above.

OBJECT OF THE INVENTION

It is an object of the present invention to substantially overcome or at least ameliorate one or more of the above disadvantages.

SUMMARY OF THE INVENTION

Accordingly, in a first aspect, the present invention provides a mandibular advancement device including:

a lower part that is releasably attachable to at least a portion of a lower jaw;

a lower flange with a lower engagement surface extending upwardly from the lower part;

an upper part that is releasably attachable to at least a portion of an upper jaw;

an upper flange with an upper engagement surface extending downwardly from the upper part; and the lower flange being connected to the lower part by a lower one way ratchet means configured to only allow uni-directional posterior movement of the lower flange relative to the lower part and/or the upper flange being connected to the upper part by an upper one way ratchet means configured to only allow uni-directional anterior movement of the upper flange relative to the upper part, wherein, when the lower part and the upper part are fitted to the jaws of a patient for use in sleep, the lower engagement surface and the upper engagement surface engage in a manner to cause anterior advancement of the lower jaw from the reflex path of opening.

In one embodiment, only the lower flange is connected to the lower part by the lower one way ratchet means and the amount of anterior advancement of the lower jaw is adjustable by the positioning of the lower flange relative to the lower part. In this embodiment, the upper flange is fixed to the upper part.

In another embodiment, only the upper flange is connected to the upper part by the upper one way ratchet means and the amount of anterior advancement of the lower jaw is adjustable by the positioning of the upper flange relative to the upper part. In this embodiment, the lower flange is fixed to the lower part.

In a further embodiment, the lower flange is connected to the lower part by the lower one way ratchet means and the upper flange is connected to the upper part by the upper one way ratchet means, and the amount of anterior advancement of the lower jaw is adjustable by the positioning of the lower flange relative to the lower part and by the positioning of the upper flange relative to the upper part.

Preferably, the lower flange includes a left said lower flange and left said lower ratchet means and a right said lower flange and a right said lower ratchet means. Preferably also, the upper flange includes a left said upper flange and left said upper ratchet means and a right said upper flange and a right said upper ratchet means.

The lower ratchet means preferably includes a lower teeth rack on the lower part and a lower ratchet tooth or teeth on the lower flange. The upper ratchet means preferably includes an upper teeth rack on the upper part and an upper ratchet tooth or teeth on the upper flange.

The lower part preferably includes a lower opening adapted to releasably receive a handle. The upper part preferably includes an upper opening adapted to releasably receive a handle.

The lower part is preferably formed from a relatively hard shell (e.g. polyamide) and a heat formable lining (e.g. polycaprolactone [PCL]). In one form, a relatively soft lining (e.g. ethylene vinyl acetate [EVA] or polyurethane) is included in the lower part, with the heat formable lining being positioned between the relatively hard shell and the relatively soft lining.

The upper part is preferably formed from a relatively hard shell (e.g. polyamide) and a heat formable lining (e.g. polycaprolactone [PCL]). In one form, a relatively soft lining (e.g. ethylene vinyl acetate [EVA] or polyurethane) is included in the upper part, with the heat formable lining being positioned between the relatively hard shell and the relatively soft lining.

In a second aspect, the present invention provides a mandibular advancement device including:

a lower part that is releasably attachable to at least a portion of a lower jaw;

a lower flange with a lower engagement surface extending upwardly from the lower part;

an upper part that is releasably attachable to at least a portion of an upper jaw;

an upper flange with an upper engagement surface extending downwardly from the upper part;

the lower part being formed from a relatively hard lower shell, a relatively soft lower lining and a heat formable lower inner lining therebetween; and the upper part being formed from a relatively hard upper shell, a relatively soft upper lining and a heat formable upper inner lining therebetween, wherein, when the lower part and the upper part are fitted to the jaws of a patient for use in sleep, the lower engagement surface and the upper engagement surface engage in a manner to cause anterior advancement of the lower jaw from the reflex path of opening.

Preferably, the shells are formed from polyamide, the heat formable inner linings from polycaprolactone [PCL] and the relatively soft linings from ethylene vinyl acetate [EVA].

In one embodiment, the lower flange is connected to the lower part by a lower one way ratchet means configured to only allow uni-directional posterior movement of the lower flange relative to the lower part. In this embodiment, the upper flange is fixed to the upper part.

In another embodiment, the upper flange is connected to the upper part by an upper one way ratchet means configured to only allow uni-directional anterior movement of the upper flange relative to the upper part. In this embodiment, the lower flange is fixed to the lower part.

In a further embodiment, the lower flange is connected to the lower part by a lower one way ratchet means configured to only allow uni-directional posterior movement of the lower flange relative to the lower part and the upper flange is connected to the upper part by an upper one way ratchet means configured to only allow uni-directional anterior movement of the upper flange relative to the upper part.

DETAILED DESCRIPTION OF THE DRAWINGS

A preferred embodiment of the invention will now be described, by way of an example only, with reference to the accompanying drawings, in which.

BRIEF DESCRIPTION OF THE PREFERRED EMBODIMENTS

Figure 1:
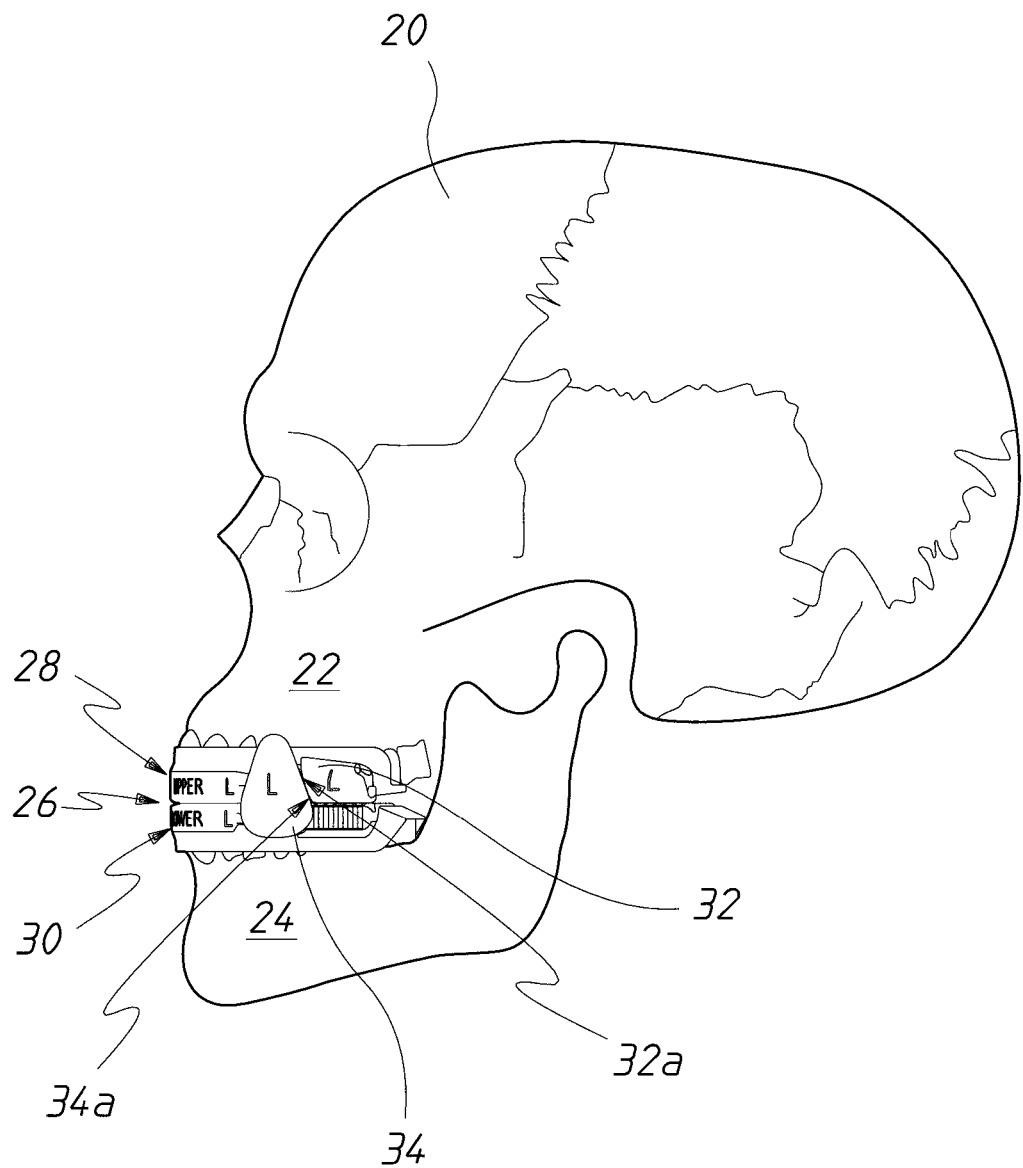
FIG. 1 is a side view of a human skull fitted with an embodiment of a mandibular advancement device, with the jaw in a closed position.
Figure 2:
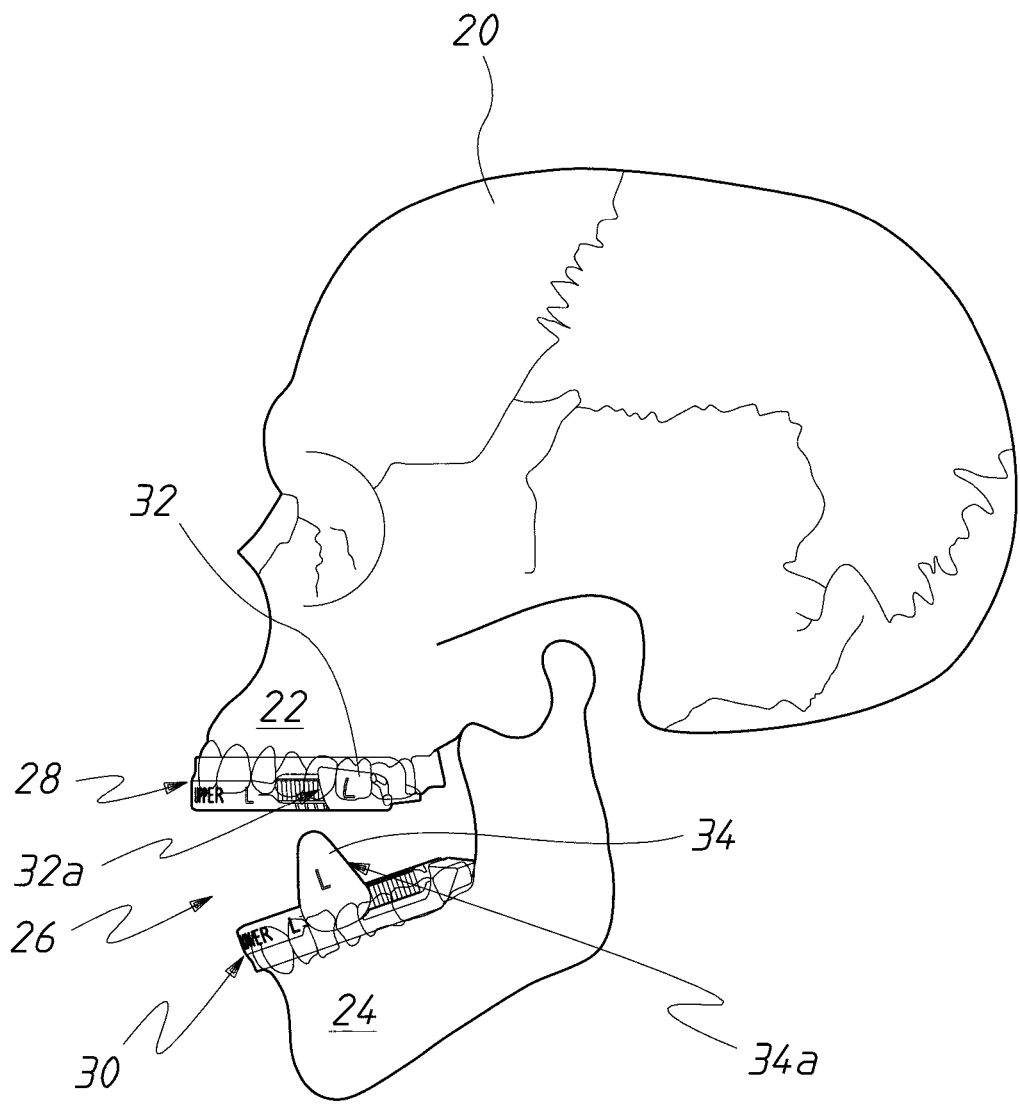
FIG. 2 shows the skull and the device of FIG. 1, with the jaw in an open position.

FIG. 1 shows a skull 20 with an upper jaw 22 and a lower jaw 24. An embodiment of a mandibular advancement device 26 is fitted to the jaws 22 and 24. The device 26 includes an upper part, in the form of an upper bite block 28, and a lower part, in the form of a lower bite block 30. The upper 28 and lower 30 bite blocks have "UPPER" and "LOWER" markings respectively thereon, together with "L" (left) and "R" (right), to assist in patient fitment. Also shown in FIGS. 1 and 2 are a left hand side upper flange 32 and a left hand side lower flange 34. As will be described in more detail below, the leading edge 32a of the flange 32 acts as an engagement surface and the leading edge 34a of the flange 34 acts as an engagement surface. A similar set of flanges, are provided on the right hand side of the bite blocks 28 and 30. The left hand flanges 32 and 34 have an "L" marking thereon to assist in patient fitment. The right hand flanges are similarly marked with an "R".

Figure 3:
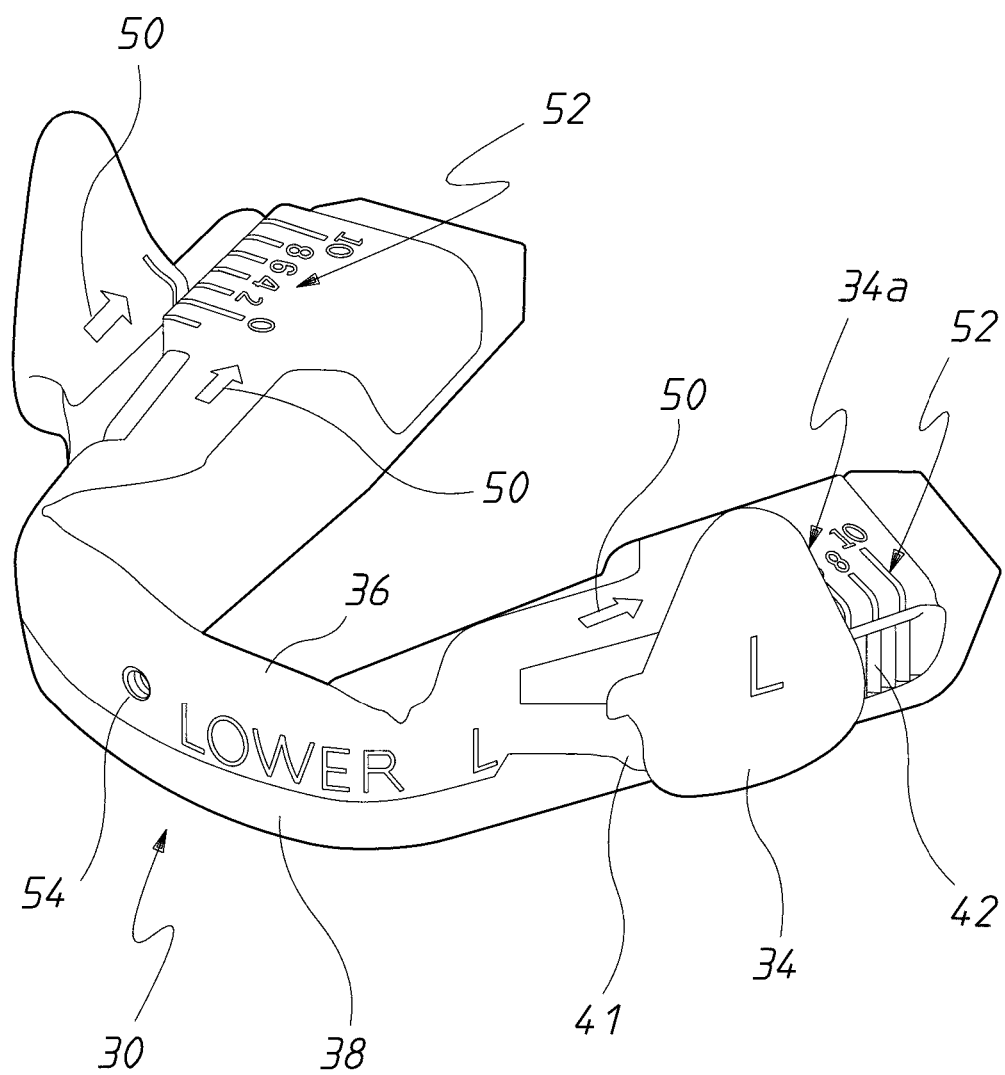
FIG. 3 is a perspective view of a lower bite block of the device shown in FIG. 1.
Figure 7:
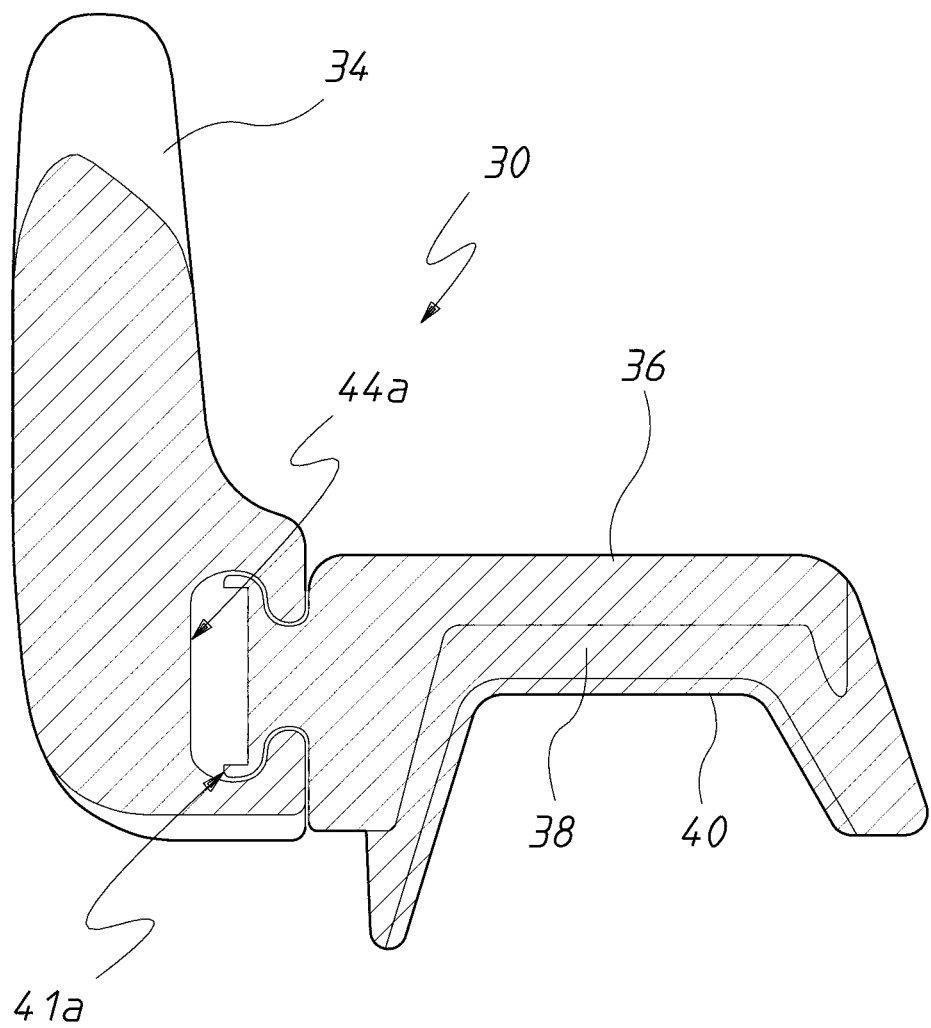
FIG. 7 is a cross sectional end view of the bite block shown in FIG. 5 along the line 7-7.

FIG. 3 shows the lower bite block 30 in isolation. The bite block 30 includes a relatively hard shell 36, injection moulded from polyamide, to which is bonded (by epoxy) a heat formable lining 38, injection moulded from PCL. As best shown in FIG. 7, the heat formable lining 38 is covered by a relatively soft lining 40, formed from EVA or polyurethane. The relatively soft lining 40 can also be formed from a heat formable material.

Figure 4:
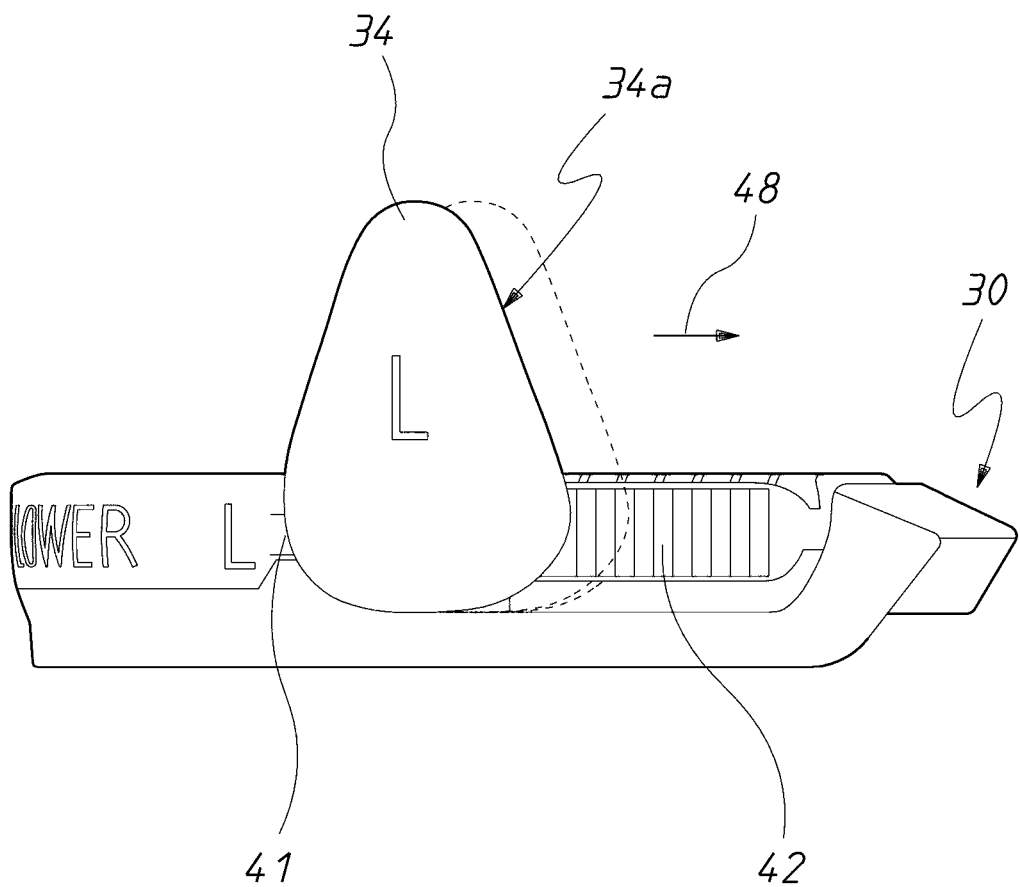
FIG. 4 is a side view of the lower bite block shown in FIG. 3.

Returning to FIG. 3, each side of the shell 36 includes a rail 41 on which is formed a teeth rack 42. As best shown in FIG. 6, the flange 34 includes three ratchet teeth 44 formed thereon. As best shown in FIG. 7, the flange 34 includes a dovetail type recess 44a which engages the like-shaped exterior 41a of the rail 41. This engagement allows relative sliding movement whilst keeping the flange 34 engaged with the rail 41. As best shown in FIG. 6, the teeth rack 42 and the ratchet teeth 44 are saw tooth in profile making them uni-directional. The construction and operation of the teeth rack 42 and ratchet teeth 44 is similar to that of a cable-tie or tie-wrap. The ratchet teeth 44 are resiliently biased towards the teeth rack 42 and pivot away from, and then back towards, the teeth rack 42, as indicated by double headed arrow 46, whilst the flange 34 is moved relative to the shell 36 in the direction of arrow 48. FIG. 4 shows that the uni-directional movement of the flange 34 is in the posterior direction, from an initial position to an advanced position (shown in phantom). To assist the user, both the flange 34 and the shell 36 have arrow indicators 50 thereon to indicate the adjustment direction (see FIG. 5).

Figure 5:
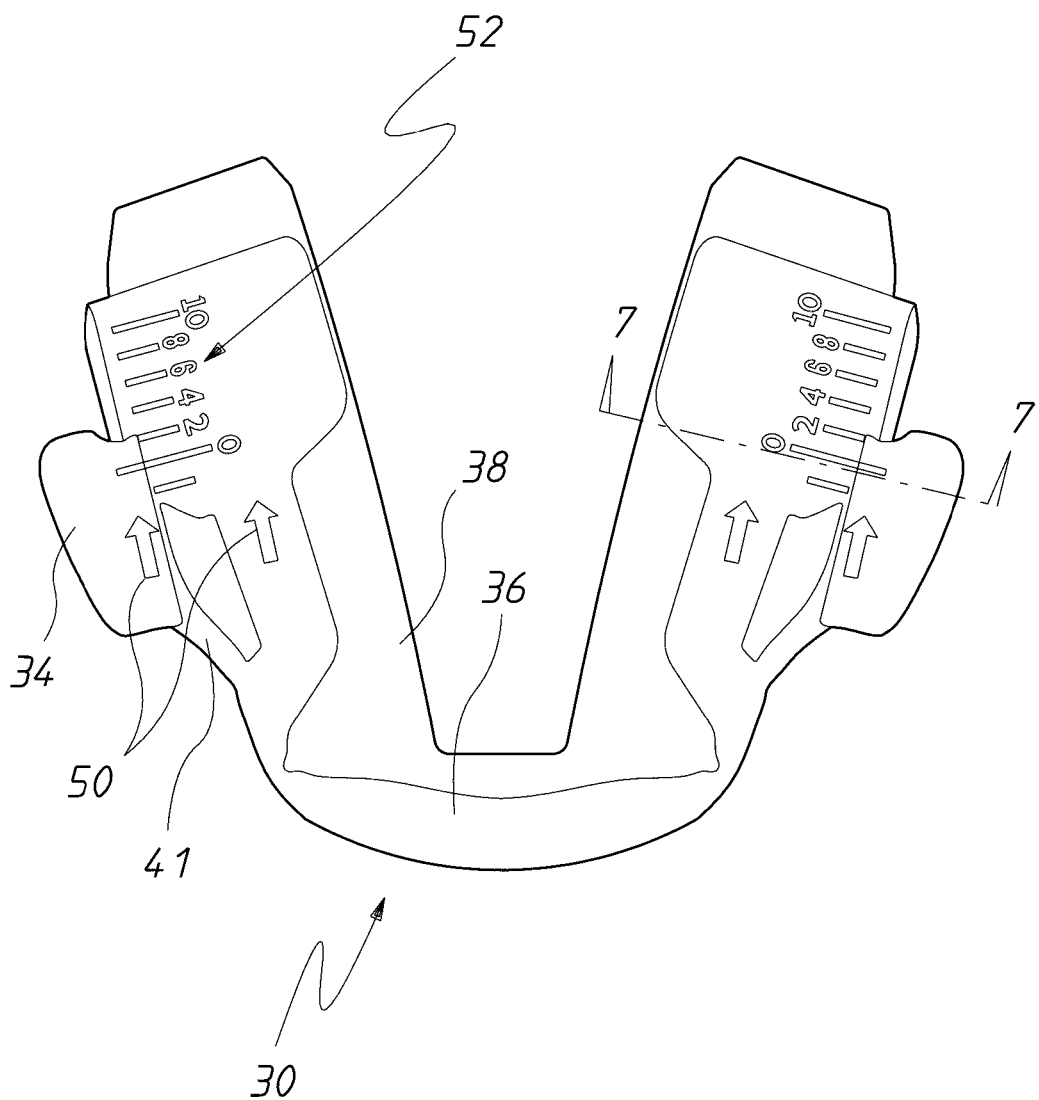
FIG. 5 is an top view of the lower bite block shown in FIG. 3.
Figure 6:
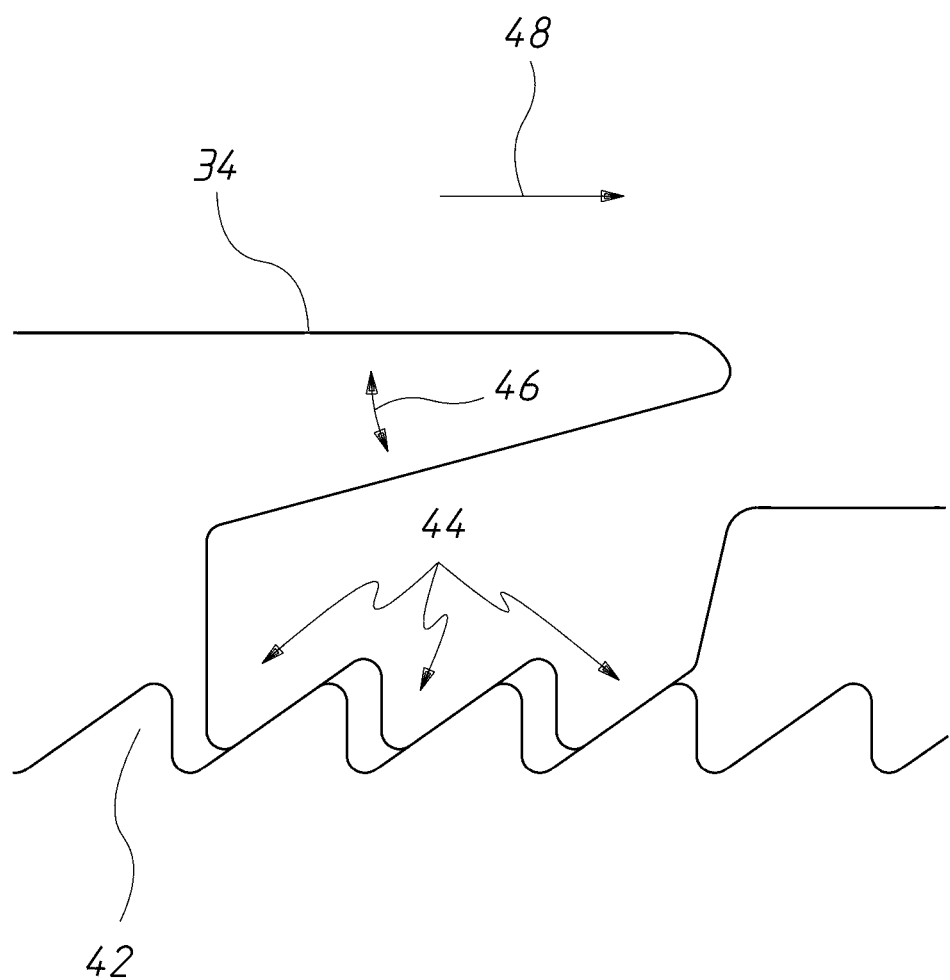
FIG. 6 is an enlarged detailed view of a teeth rack and a ratchet used in the bite block shown in FIG. 3.

As best shown in FIG. 5, a numerical indicator 52 of the amount of adjustment selected by the user is also shown on the top surface of the shell 36. Each incremental movement of adjustment relative to the shell 36 produces a "click" sound and is equal to about 1 mm of movement. If the patient positions the flange 34 past an intended position, the flange 34 can be simply slid off the end of the rail 41 by further movement in the direction of the arrow indicators 50 and then reinstalled at the initial position shown in FIG. 5 for readjustment.

Figure 14:
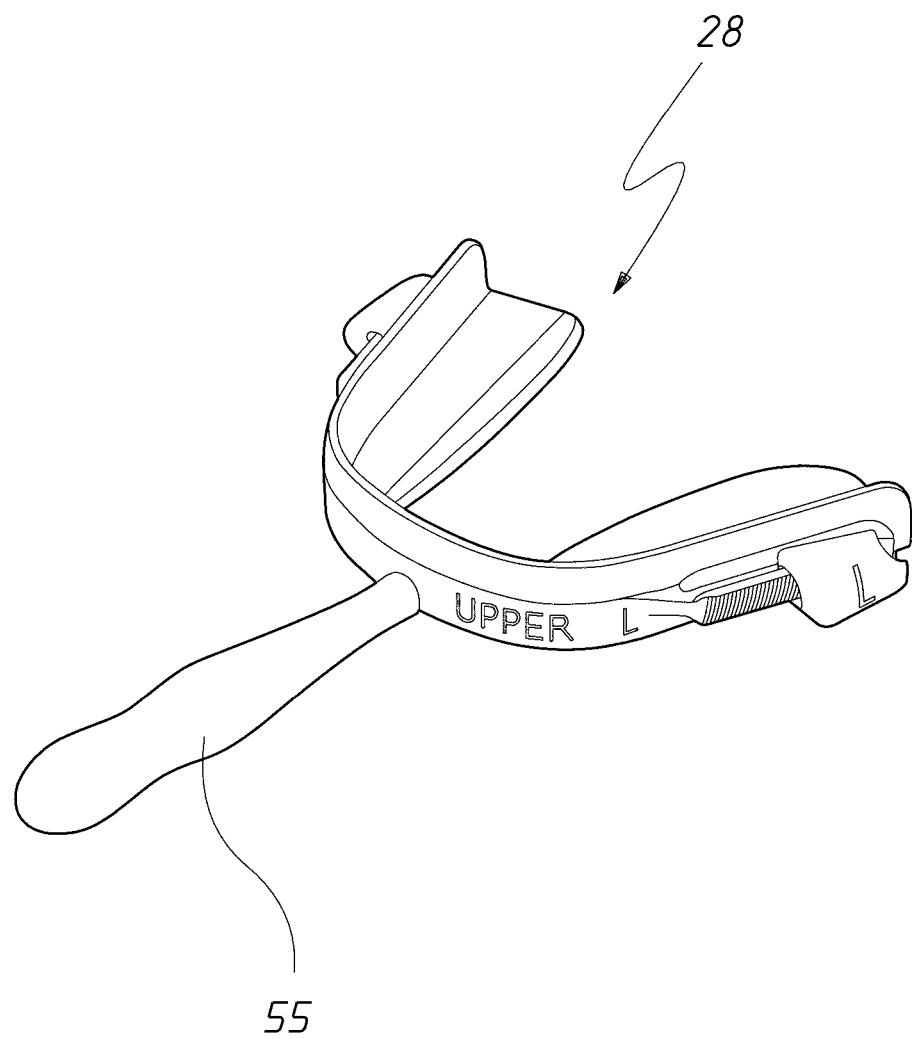
FIG. 14 shows the upper bite block shell of FIG. 8 connected to a handle.

FIG. 3 also shows the threaded hole 54 in the front of the shell 36, used to fit a handle 55 (see FIG. 14).

Figure 8:
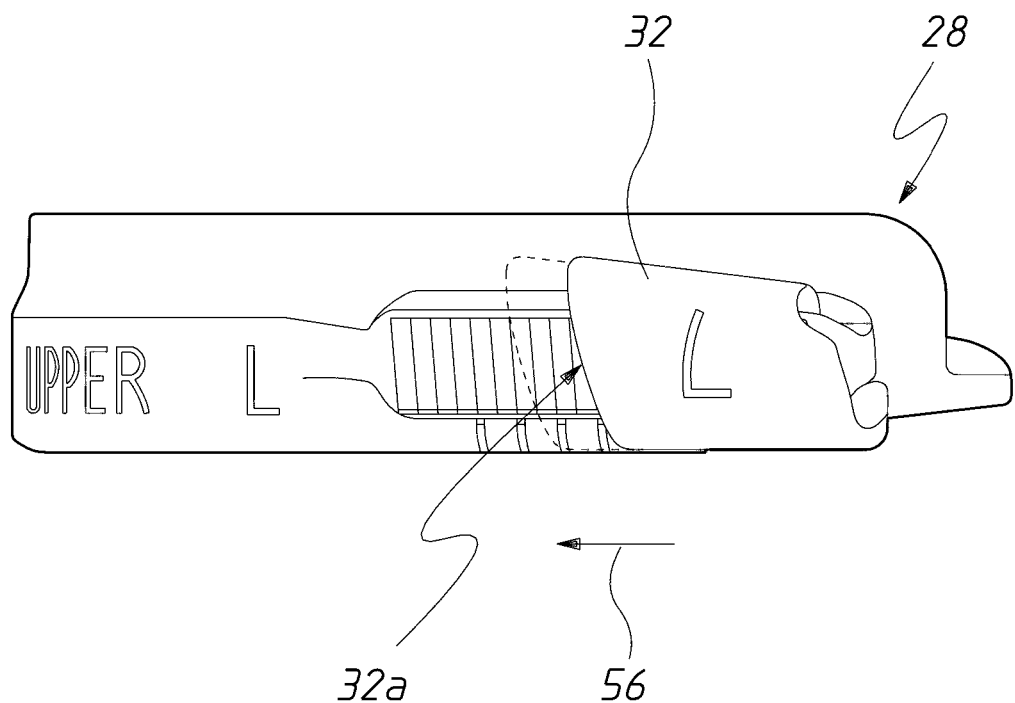
FIG. 8 is a side view of an upper bite block of the device shown in FIG. 1.
Figure 9:
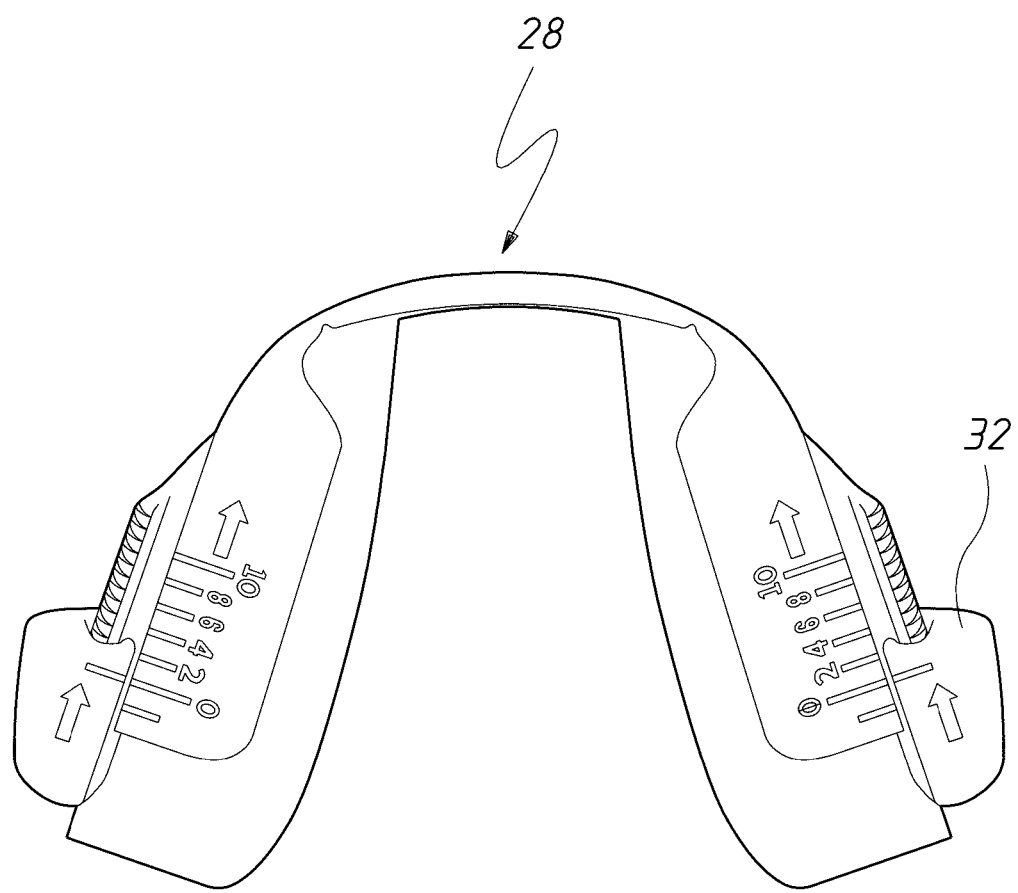
FIG. 9 is a underside view of the upper bite block shown in FIG. 8.

FIGS. 8 and 9 show the upper bite block 28, which has a similar shell and liner construction as the lower bite block 30 previously described. The upper bite block 28 also has a similar uni-directional ratchet arrangement for the upper flange 32, as those previously described. The shell of the upper bite block 28 also contains similar numerical and directional indicators on its bottom surface. FIG. 8 also shows that the upper flange 32 can be moved only in the anterior direction, indicated by arrow 56, from an initial position shown to an advanced position (shown in phantom).

Figure 10:
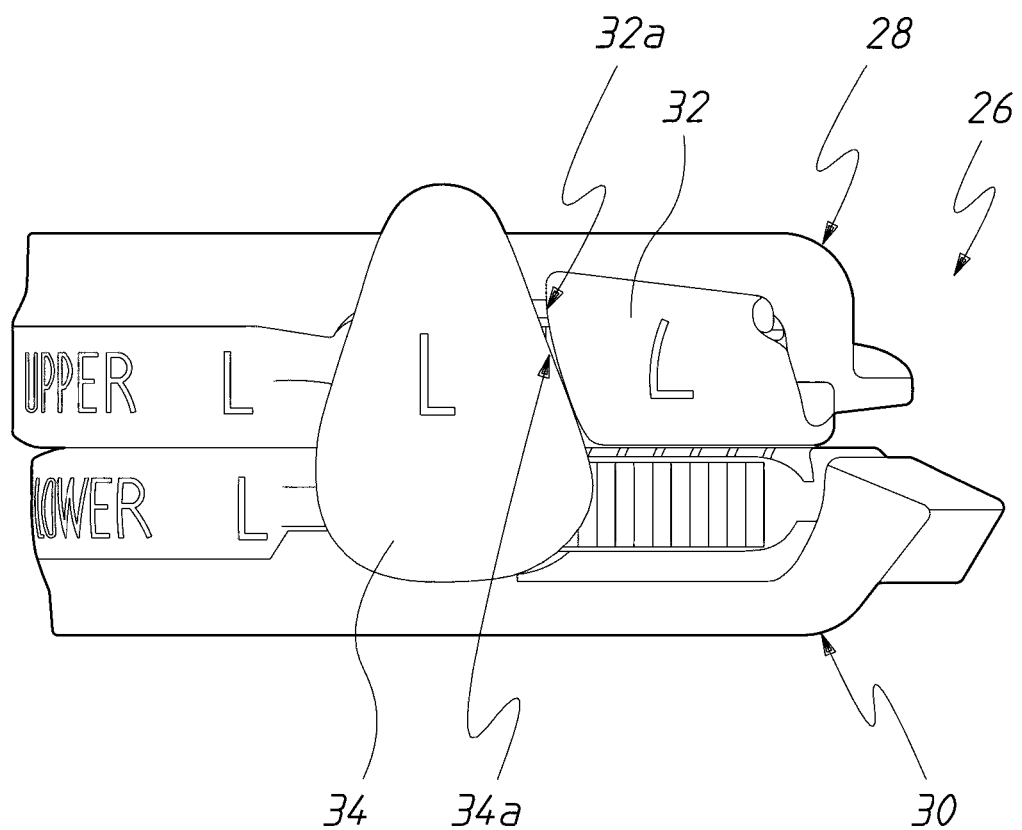
FIG. 10 is a side view of the device shown in FIG. 1 adjusted to provide a minimum amount of mandibular advancement.

FIG. 10. shows the upper and lower bite blocks 28, 30 positioned for use with one another with the leading edges 32a, 34a of the flanges abutting and engaged with one another. In FIG. 10, both of the flanges 32, 34 are at the beginning of their respective ranges of jaw advancement.

The use of the device 26 will now be described. As shown in FIG. 14, the handle 55 is screwed to the hole in the upper bite block 28. The upper bite block 28 is then placed in boiling water until the heat formable lining 38 softens. If the soft lining 40 is also formed from a mouldable material then it will also soften. The bite block 28 is then retrieved from the water by the handle 55. Using the handle the bite block 28 is positioned in the patient's mouth. The patient then bites down to form an impression of their teeth and jaw in the mouldable material of the heat formable lining 38. The material of the heat formable lining 38 is then allowed to cool so as to retain the patient's impression therein. If used, the heat mouldable material of the soft lining 40 also retains the patient's impression therein once cooled. The handle 55 is then removed from the upper bite block 28 and a similar process is carried out for the lower bite block 30.

The upper 32 and lower 34 flanges are assembled with the upper 28 and lower 30 bite blocks respectively, by sliding them to the rail 41 until the ratchet teeth 44 make initial engagement with the teeth rack 42. This initial engagement is indicated by an audible click or clicks and a slight resistance to movement in the direction of the arrow 48 (lower) or 56 (upper). This initial assembly is shown in FIG. 10 and provides a minimum amount of mandibular advancement of the patient's lower jaw. The device 26 is then fitted to the patient's jaw and, by trial and error, the flanges 32, 34 can be advanced in their respective single directions in order to adjust the mandibular advancement of the lower jaw to the desired amount. The leading edges 32a, 34a of the upper and lower flanges 32, 34 engage and abut against one another causing the desired amount of mandibular advancement to be maintained.

Figure 11:
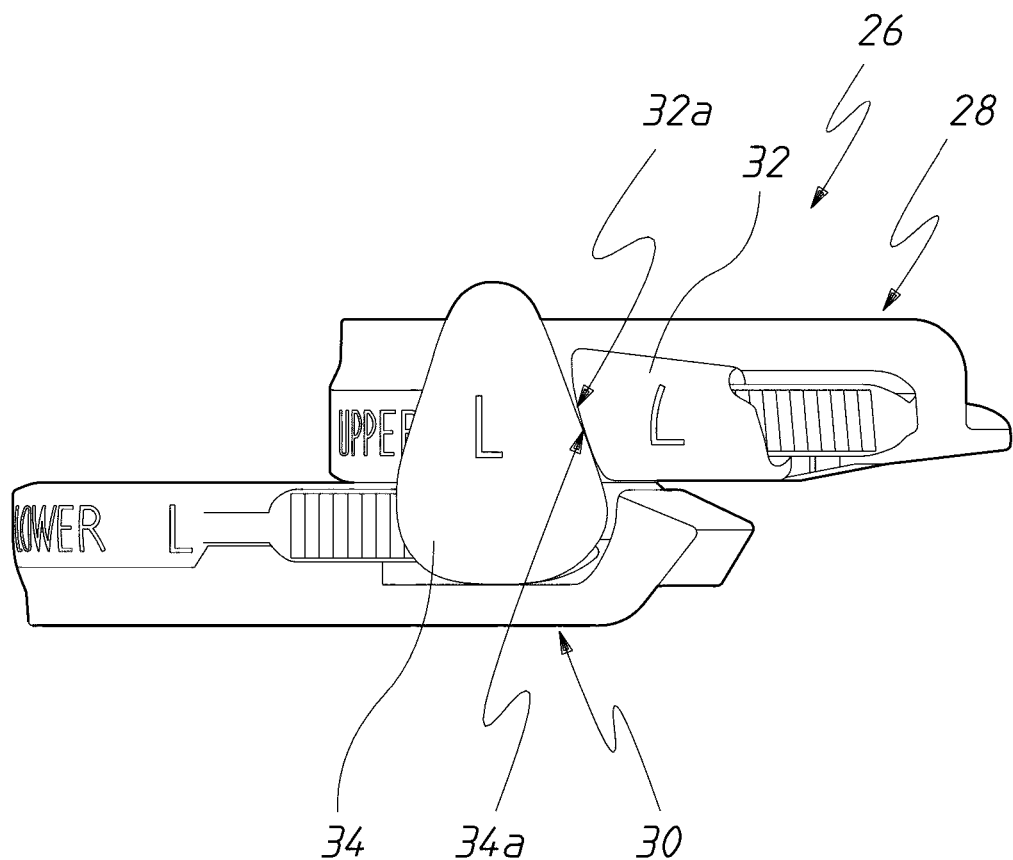
FIG. 11 shows the device of FIG. 10 adjusted to provide a maximum amount of mandibular advancement.

FIG. 11 shows the flanges 32, 34 adjusted to provide a maximum amount of mandibular advancement.

Figure 12:
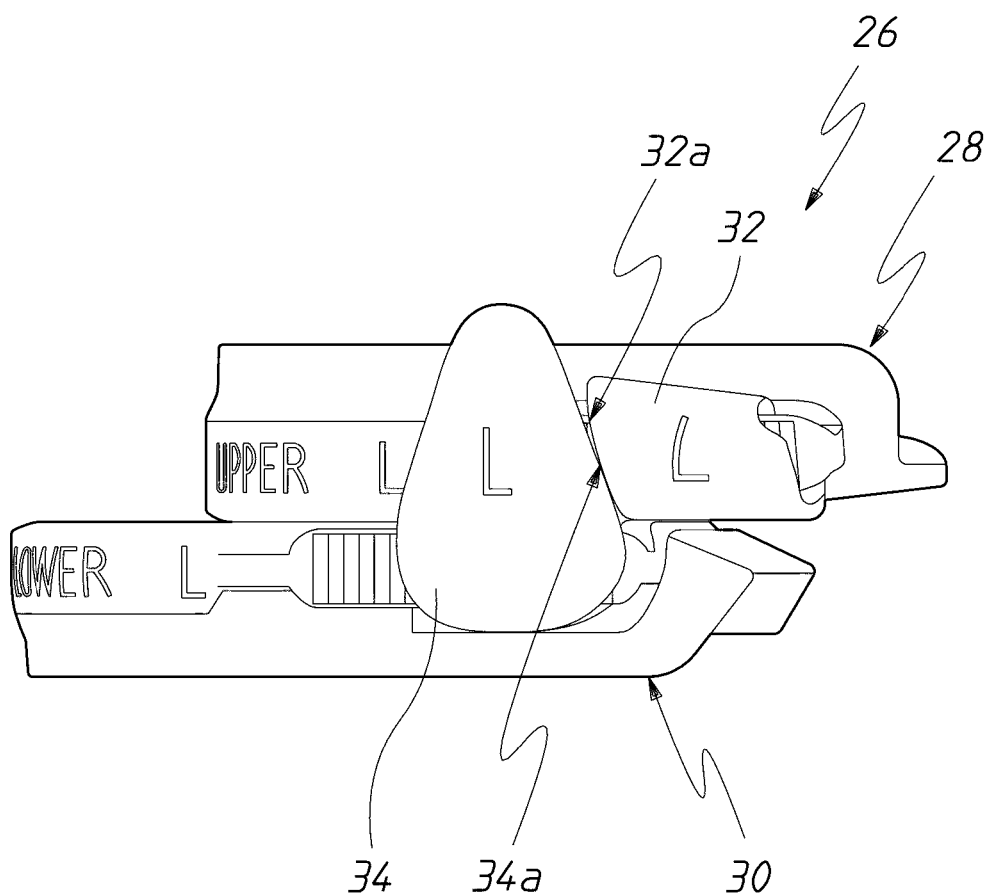
FIG. 12 shows the device of FIG. 10 adjusted to provide an intermediate amount of mandibular advancement.
Figure 13:
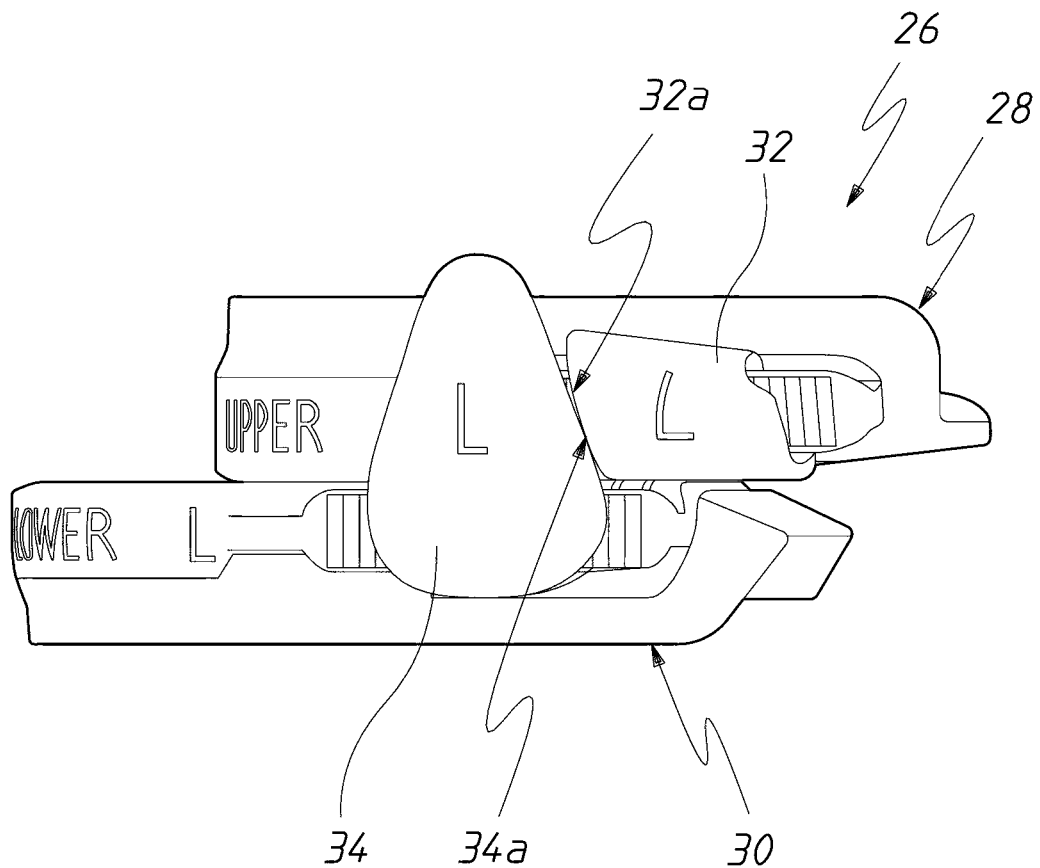
FIG. 13 shows the device of FIG. 10 adjusted to provide an intermediate amount of mandibular advancement.

FIGS. 12 and 13 each show a similar intermediate amount of mandibular advancement and also demonstrate that a similar amount of mandibular advancement can be achieved whilst positioning the flanges 32, 34 in different locations.

The device 26 retains the desired amount of mandibular advancement as the lower flange 34 can only move relative to the lower bite block 30 in an anterior direction (i.e. it cannot move in the posterior direction) and the upper flange 32 can only move relative to the upper bite block 28 in the posterior direction (i.e. it cannot move in the anterior direction).

The device 26 has numerous advantages. Firstly, the device is of the universal fitment type and is thus suited for mass production at a relatively low cost compared to custom devices. Secondly, the device allows the patient's jaw to be opened, allowing speaking, yawning and drinking whilst wearing the device. Thirdly, the adjustment devices are contained within the patient's mouth thereby allowing a lip seal to be maintained and avoiding the patient's mouth drying out during sleep. Fourthly, the adjustment of the position of the flanges and thus the mandibular advancement is both relatively simple and also intuitive. More particularly, the various components of the device are clearly marked and the flanges can only be assembled for use in their intended position and direction. There are also clear and easy to read indicators of the positions selected and there are no locks or other smaller or secondary components which need to be manipulated. The device also allows the anterior/posterior position of the flanges in the mouth to be adjusted for maximum patient comfort, independent of the desired amount of the lower jaw advancement (see FIGS. 12 and 13). The left hand flanges can also be positioned independently of the right hand flanges, again for maximum patient comfort. The advancement of one side of the jaw can be adjusted differently to the other side of the jaw, if required to best suit the patient's jaw anatomy. Finally, the soft coating over the mouldable lining increases patient comfort due to it providing a soft material in direct contact with the patient's teeth. The soft coating acts as a shock absorber, helps in equal dissipation of occlusal stresses and is compressed during function thereby increasing retention and minimizing trauma by preventing a direct contact of hard material such as the hard shell or the formed heat formable lining.

Although the invention has been described with reference to a preferred embodiment, it will be appreciated by those persons skilled in the art that the invention may be embodied in many other forms.

The invention claimed is:

1. A mandibular advancement device including:
a lower part that is configured to be releasably attached to at least a portion of a lower jaw of a patient;
a lower flange with a lower engagement surface extending upwardly from the lower part;
an upper part that is configured to be releasably attached to at least a portion of an upper jaw of the patient;
an upper flange with an upper engagement surface extending downwardly from the upper part;
the lower flange being connected to the lower part by a lower one way ratchet means configured to only allow uni-directional posterior movement of the lower flange relative to the lower part, wherein the lower one way ratchet means includes a lower teeth rack on the lower part and a lower ratchet tooth or teeth on the lower flange, wherein the lower teeth rack includes a first end provided at a posterior region of the lower part and an oppositely disposed second end provided at an anterior region of the lower part, wherein the lower flange is configured to disengage the lower part by sliding the lower ratchet tooth or teeth along the lower teeth rack in the posterior direction until the lower flange slides off the first end of the lower teeth rack; and
the upper flange being connected to the upper part by an upper one way ratchet means configured to only allow uni-directional anterior movement of the upper flange relative to the upper part, wherein the upper one way ratchet means includes an upper teeth rack on the upper part and an upper ratchet tooth or teeth on the upper flange, wherein the upper teeth rack includes a first end provided at an anterior region of the upper part and an oppositely disposed second end provided at a posterior region of the upper part, wherein the upper flange is configured to disengage the upper part by sliding the upper ratchet tooth or teeth along the upper teeth rack in the anterior direction until the upper flange slides off the first end of the upper teeth rack,
wherein, when the lower part and the upper part are fitted to the upper jaw and the lower jaw of the patient for use in sleep, the lower engagement surface and the upper engagement surface are configured to engage one another to cause anterior advancement of the lower jaw from a reflex path of opening.

2. The mandibular advancement device as claimed in claim 1, wherein only the lower flange is connected to the lower part by the lower one way ratchet means and the device is configured such that an amount of anterior advancement of the lower jaw is adjustable by positioning of the lower flange relative to the lower part.

3. The mandibular advancement device as claimed in claim 2, wherein the upper flange is fixed to the upper part.

4. The mandibular advancement device as claimed in claim 1, wherein only the upper flange is connected to the upper part by the upper one way ratchet means and the device is configured such that an amount of anterior advancement of the lower jaw is adjustable by positioning of the upper flange relative to the upper part.

5. The mandibular advancement device as claimed in claim 4, wherein the lower flange is fixed to the lower part.

6. The mandibular advancement device as claimed in claim 1, wherein the lower part is formed from a relatively hard shell and a heat formable lining.

7. The mandibular advancement device as claimed in claim 6, wherein a relatively soft lining is included in the lower part, with the heat formable lining being positioned between the relatively hard shell and the relatively soft lining.

8. The mandibular advancement device as claimed in claim 1, wherein the upper part is formed from a relatively hard shell and a heat formable lining.

9. The mandibular advancement device as claimed in claim 8, wherein a relatively soft lining is included in the upper part, with the heat formable lining being positioned between the relatively hard shell and the relatively soft lining.

10. The mandibular advancement device as claimed in claim 1, wherein the device is configured such that an amount of anterior advancement of the lower jaw is adjustable by positioning of the lower flange relative to the lower part and by positioning of the upper flange relative to the upper part.

11. The mandibular advancement device as claimed in claim 1, wherein the device includes a left said lower flange, a left said lower one way ratchet means, a right said lower flange, and a right said lower one way ratchet means.

12. The mandibular advancement device as claimed in claim 1, wherein the device includes a left said upper flange, a left said upper one way ratchet means, a right said upper flange, and a right said upper one way ratchet means.

13. The mandibular advancement device as claimed in claim 1, wherein the lower part includes a lower opening adapted to releasably receive a handle.

14. The mandibular advancement device as claimed in claim 1, wherein the upper part includes an upper opening adapted to releasably receive a handle.

15. A mandibular advancement device including:
a lower part that is configured to be releasably attached to at least a portion of a lower jaw of a patient;
a lower flange with a lower engagement surface extending upwardly from the lower part;
an upper part that is configured to be releasably attached to at least a portion of an upper jaw of the patient;
an upper flange with an upper engagement surface extending downwardly from the upper part;
the lower flange being connected to the lower part by a lower one way ratchet means configured to only allow uni-directional posterior movement of the lower flange relative to the lower part, wherein the lower one way ratchet means includes a lower teeth rack on the lower part and a lower ratchet tooth or teeth on the lower flange, wherein the lower teeth rack includes a first end provided at a posterior region of the lower part and an oppositely disposed second end provided at an anterior region of the lower part, wherein the lower flange is configured to disengage the lower part by sliding the lower ratchet tooth or teeth along the lower teeth rack in the posterior direction until the lower flange slides off the first end of the lower teeth rack; and
the upper flange being connected to the upper part by an upper one way ratchet means configured to only allow uni-directional anterior movement of the upper flange relative to the upper part, wherein the upper one way ratchet means includes an upper teeth rack on the upper part and an upper ratchet tooth or teeth on the upper flange, wherein the upper teeth rack includes a first end provided at an anterior region of the upper part and an oppositely disposed second end provided at a posterior region of the upper part, wherein the upper flange is configured to disengage the upper part by sliding the upper ratchet tooth or teeth along the upper teeth rack in the anterior direction until the upper flange slides off the first end of the upper teeth rack, the lower part being formed from a relatively hard lower shell, a relatively soft lower lining and a heat formable lower inner lining therebetween; and the upper part being formed from a relatively hard upper shell, a relatively soft upper lining and a heat formable upper inner lining therebetween, wherein, when the lower part and the upper part are fitted to the upper jaw and the lower jaw of the patient for use in sleep, the lower engagement surface and the upper engagement surface are configured to engage one another to cause anterior advancement of the lower jaw from a reflex path of opening.

16. The mandibular advancement device as claimed in claim 15, wherein the relatively hard upper shell and relatively hard lower shell are formed from polyamide, the heat formable upper inner lining and heat formable lower inner lining are formed from polycaprolactone [PCL], and the relatively soft upper lining and relatively soft lower lining are formed from ethylene vinyl acetate [EVA].

* * * * *